(12) United States Patent
Xiao et al.

(10) Patent No.: US 10,744,173 B2
(45) Date of Patent: Aug. 18, 2020

(54) TRADITIONAL CHINESE MEDICINE COMPOSITIONS FOR ALLEVIATING STRESS

(71) Applicant: Infinitus (China) Company Ltd., Jiang Men (CN)

(72) Inventors: Lingyun Xiao, Jiang Men (CN); Renhuai Cong, Jiang Men (CN); Minghua Hu, Jiang Men (CN); Yuanyuan Wang, Jiang Men (CN); Fangli Ma, Jiang Men (CN); Chung Wah Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 80 days.

(21) Appl. No.: 15/882,477

(22) Filed: Jan. 29, 2018

(65) Prior Publication Data
US 2018/0296618 A1   Oct. 18, 2018

(30) Foreign Application Priority Data

Apr. 14, 2017   (CN) .......................... 2017 1 0244073
Nov. 10, 2017   (CN) .......................... 2017 1 1104390

(51) Int. Cl.
| | |
|---|---|
| *A61K 36/258* | (2006.01) |
| *A61K 36/9062* | (2006.01) |
| *A61K 36/71* | (2006.01) |
| *A61K 36/704* | (2006.01) |

(52) U.S. Cl.
CPC .......... *A61K 36/258* (2013.01); *A61K 36/704* (2013.01); *A61K 36/71* (2013.01); *A61K 36/9062* (2013.01); *A61K 2236/331* (2013.01)

(58) Field of Classification Search
None
See application file for complete search history.

(56) References Cited

U.S. PATENT DOCUMENTS

2016/0140314 A1 *   5/2016   Karchmer ........... G06F 19/3456
                                                         600/33

FOREIGN PATENT DOCUMENTS

| CN | 101332264 | * | 12/2008 |
| CN | 101711852 | * | 4/2011 |
| CN | 103989164 | * | 8/2014 |
| CN | 105362660 | * | 3/2016 |
| CN | 105535765 | * | 5/2016 |

* cited by examiner

*Primary Examiner* — Ralph J Gitomer
(74) *Attorney, Agent, or Firm* — Fox Rothschild LLP

(57) ABSTRACT

The present invention relates to the technical field of healthcare product, and in particular relates to a traditional Chinese medicine composition having a function of regulating emotions, a process for preparing the same, and a product thereof. It was found that the composition of the present invention had effects of nourishing liver and kidney, regulating Yin and Yang, tonifying Qi and nourishing blood, regulating emotions, and protecting the function of autonomic nerve, and could improve pressure-induced anxiety and depression, inattention, poor spirit, dispirited, learning and memory capacity decline, etc. The invention has the advantages of specificity and remarkable effect, and it uses all natural medicinal and edible plants as raw materials, the combination of which is simple, safe and stable, and is suitable for long-term use.

3 Claims, No Drawings

TRADITIONAL CHINESE MEDICINE COMPOSITIONS FOR ALLEVIATING STRESS

All patent and non-patent reference cited in the application, are also hereby incorporated by reference in their entity. The present application claims the benefit of CN201710244073.9 filed on Apr. 14, 2017, and CN201711104390.7 filed on Nov. 10, 2017, the contents of which are hereby incorporated by reference.

FIELD OF THE INVENTION

The present invention relates to the technical field of health-care product, and in particular relates to a traditional Chinese medicine composition having a function of regulating emotions, a process for preparing the same, and a product thereof.

BACKGROUND OF THE INVENTION

With the socio-economic development, pressure from work and life gradually increased, anxiety, depression, insomnia and other mental health problems become increasingly prominent. Dating back to the "Nei Jing (the Canon of Internal Medicine)" period, it was recognized that environmental factors, adverse mental stimulation could cause mental and physical illness. Human emotional activities or living habits, which is contrary to the degree of regulation over the body itself, will directly damage the organs, Qi, blood, Yin and Yang, and thus it will cause disease. Disease arises from the inside, and it's mainly caused by the seven emotions, eating disorder, work and rest imbalance and other factors. It is believed in Traditional Chinese Medicine that emotional distress is not only the main symptom but also the root cause of melancholia. It was recorded in the book of "The root cause of disease chapter of Nei Jing (the Canon of Internal Medicine) Plain Questions" that worrying and overthinking could lead to heart damage. In the book of "Treatise on Three Categories of Pathogenic Factors", the author, Chen Yan, pointed out for the first time that the seven emotions were normal human mental activities, but the excessive seven emotions led to organs stagnation, abnormal accumulation and distribution of blood and body fluid, and therefore induced emotional diseases.

Liver controls conveyance and dispersion, regulates Qi activity, and regulates emotions, if the long-term repeated mental stimulation exceeds the tolerance capacity of the body, it will affect the conveyance and dispersion of liver, liver fails to act freely, and then leads to liver-Qi stagnation. Qi depression transforms into fire, and followed by body fluid concentrates into phlegm and disturbs clear orifices, and thus the patients appear abnormal mental activity, mental depression, and memory loss and so on. Liver depression transforms into fire to disturb heart vessel, and then the patients feel upset, difficulty fall asleep and so on. Liver depression transforms into phlegm, phlegm fire disturbs gallbladder, gallbladder controls decision, so the symptoms of the patients are bradykinesia and have poor decision making abilities and so on. Heart controls blood circulation and mental activities, and spleen controls transport and transformation which is the source of Qi-Blood. If people think too much and the mental pressure of whom is too large, it results in spleen damage, and followed by Qi-Blood deficiency and lacking body nourishment which controlled by transport and transformation of spleen, then the patients appear anorexia, emaciation, and weak limbs, and it also results in the Heart-Blood damage, and followed by Heart-Blood deficiency and lacking mental nourishment which controlled by heart, then the patients appear palpitation, amnesia, insomnia and dreaminess. Kidney is the foundation of the Yin liquid of whole body. Yin liquid has the effect of making the human body moist and quiet, and it can moist Heart-Yin, inhibit Liver-Yang, and supply the substance basis of the organs and brain. If Qi depression transforms into fire and damages Yin liquid, the result is that Yang is out of control, Yang flourishes while Yin declines, Yin deficiency generates interior heat, and thus the patients appear the symptoms such as palpitation which caused by heart and mental disturbance. Brain is the sea of marrow, if the depressive state is unhealed for a long period of time, then primordial spirit lacks of nourishment, and the essence transformation is not enough, which result in "brain spin and ears ring, lower leg ache and veiling dizziness, loss of vision, slack thus lying".

To date, western medicine still has no effective medicine for pressure-induced anxiety and depression, inattention, poor spirit, dispirited, learning and memory capacity decline, etc. Only after the above symptoms developing to the disease state, some sedative hypnosis, anxiolytic and antidepressant drugs can be used to treat these diseases, which can easily lead to residual effect, withdrawal reaction, dependence and addiction and other side effects.

SUMMARY OF THE INVENTION

In view of this, the present invention provides a traditional Chinese medicine composition having a function of regulating emotions, a process for preparing the same, and a product thereof. The traditional Chinese medicine composition uses all natural medicinal and edible plants as raw materials, which is safe and stable, and has a significant effect on regulating emotions.

To achieve the objectives of the invention, the present invention provides the following technical solutions:

The present invention provides a traditional Chinese medicine composition having a function of regulating emotions, which is made from the following herbal materials in specified portions by weight:

10-100 portions of ginseng, 10-100 portions of Radix paeoniae Alba, 10-100 portions of Tree Peony Bark, 10-100 portions of Sharpleaf Galangal Fruit, and 10-100 portions of Radix Polygonum multiflorum Preparata.

The raw materials of the present compositions are all medicinal and edible plants. Ginseng has a natural flavor of sweetness, mild bitterness, and warm and natured in nature, belongs to Spleen, Lung, and Heart Channels. Its effect is for tonifying Qi, relieving depletion, promoting the secretion of saliva and body fluid, soothing the nerves, and nootropic. Ginseng, as recorded in the "Herbal Classic", has the effect of mainly filling the five internal organs, soothing the nerves, antispastic, removing evil, improving eyesight, making the mood better, and nootropic. It also has the effect of relieving cough and asthma, dredging blood vessels and meridians, purging fire and nourishing Yin, and supplementing Yang, according to the "Materia Medica Companion".

Radix paeoniae Alba, is the peeled dry roots of Paeonia lactiflora Pall., which is the plant of Ranunculaceae. It has a natural flavor of mild cold, bitterness, and sour, belongs to Liver, Spleen Channels. Its effect is for soothing the liver to relieve pain, nourishing blood to regulate menstruation, convergencing Yin and antiperspirant. It is used for treating headache and dizziness, blood deficiency and etiolation, etc.

Tree Peony Bark, is the dry root barks of Paeonia suffruticosa Andr., which is the plant of Ranunculaceae. It has a natural flavor of Bitterness, Cold, belongs to Liver, Kidney Channels. Its effect is for clearing heat and cooling blood, and promoting circulation and removing stasis. It is used for treating warm toxin with skin eruption, hematemesis, night fever abating at dawn, no sweat osteopyrexia, dysmenorrhea and amenorrhea, carbuncle swollen sore, fall into pain, etc. It was initially recorded in the "Shen Nong's Herbal Classic" and recorded as: its effect was for nourishing Yin for lowering fire, removing freckles, improving the impairment in throat, making urine easy and smooth, and treating blood stasis. The descendants treated ministerial fire specially with Amur Cork Tree, but they didn't know that the efficacy of Tree Peony Bark was better. Tree Peony Bark with red flowers had dredging effect, while Tree Peony Bark with white flowers had nourishing effect, few people knew the difference between the two, thus it should be used separately.

Sharpleaf Galangal Fruit, is the mature fruits of Alpinia oxyphylla Miq., which is the herbaceous plant of Zingiberaceae. Its effect is for reinforcing kidney to strengthen essence, tuning brain, and soothing nerves. Modern pharmacological studies have shown that Alpinia oxyphylla Miq. has neurological protection, sedative hypnosis, improved memory function and other significant biological activities.

Radix Polygonum multiflorum Preparata, is the processed product of the dried tubers of Fallopia multiflora (Thunb.) Harald., which the plant of Polygonaceae. It has little odor, and a flavor of mild sweetness and bitterness, belongs to Liver, Heart, and Kidney Channels. Its effect is for nourishing liver and kidney, benefiting essence and blood, blacking beard and hair, and strengthening the bones and muscles. It is used for treating blood deficiency and etiolation, dizziness and tinnitus, premature graying hair, and soreness and weakness of waist and knees, etc. Modern research found that Radix Polygonum multiflorum Preparata has a certain effect on depression and blood deficiency, and can improve the learning and memory ability of the dementia rats.

The present invention is based on the traditional Chinese medicine theory and made from medicinal and edible raw materials, which are selected by the famous old Chinese medicines according to several decades of clinical experience. After repeated screening and verification by modern pharmacological research methods, it was found that the composition had effects of nourishing liver and kidney, regulating Yin and Yang, tonifying Qi and nourishing blood, and regulating emotions, and could improve pressure-induced anxiety and depression, inattention, poor spirit, dispirited, learning and memory capacity decline, etc. The invention has the advantages of specific, remarkable and better effect than the single agent, and has synergistic effect, and it uses all natural medicinal and edible plants as raw materials, the combination of which is simple, safe and stable, and is suitable for long-term use.

Preferably, the traditional Chinese medicine composition is made from the following raw materials in specified portions by weight:

20-80 portions of ginseng, 20-80 portions of Radix paeoniae Alba, 20-80 portions of Tree Peony Bark, 20-80 portions of Sharpleaf Galangal Fruit, and 20-80 portions of Radix Polygonum multiflorum Preparata.

Preferably, the traditional Chinese medicine composition is made from the following raw materials in specified portions by weight:

30-70 portions of ginseng, 30-70 portions of Radix paeoniae Alba, 30-70 portions of Tree Peony Bark, 30-70 portions of Sharpleaf Galangal Fruit, and 30-70 portions of Radix Polygonum multiflorum Preparata.

Preferably, the traditional Chinese medicine composition is made from the following raw materials in specified portions by weight:

40-60 portions of ginseng, 40-60 portions of Radix paeoniae Alba, 40-60 portions of Tree Peony Bark, 40-60 portions of Sharpleaf Galangal Fruit, and 40-60 portions of Radix Polygonum multiflorum Preparata.

In a specific embodiment provided by the present invention, the traditional Chinese medicine composition is made from the following raw materials in specified portions by weight: 60 portions of ginseng, 60 portions of Radix paeoniae Alba, 60 portions of Tree Peony Bark, 45 portions of Sharpleaf Galangal Fruit, and 45 portions of Radix Polygonum multiflorum Preparata.

In another specific embodiment provided by the present invention, the traditional Chinese medicine composition is made from the following raw materials in specified portions by weight: 80 portions of ginseng, 80 portions of Radix paeoniae Alba, 80 portions of Tree Peony Bark, 20 portions of Sharpleaf Galangal Fruit, and 20 portions of Radix Polygonum multiflorum Preparata.

In another specific embodiment provided by the present invention, the traditional Chinese medicine composition is made from the following raw materials in specified portions by weight: 50 portions of ginseng, 50 portions of Radix paeoniae Alba, 50 portions of Tree Peony Bark, 50 portions of Sharpleaf Galangal Fruit, and 50 portions of Radix Polygonum multiflorum Preparata.

In another specific embodiment provided by the present invention, the traditional Chinese medicine composition is made from the following raw materials in specified portions by weight: 40 portions of ginseng, 40 portions of Radix paeoniae Alba, 40 portions of Tree Peony Bark, 60 portions of Sharpleaf Galangal Fruit, and 60 portions of Radix Polygonum multiflorum Preparata.

In another specific embodiment provided by the present invention, the traditional Chinese medicine composition is made from the following raw materials in specified portions by weight: 60 portions of ginseng, 60 portions of Radix paeoniae Alba, 60 portions of Tree Peony Bark, 40 portions of Sharpleaf Galangal Fruit, and 60 portions of Radix Polygonum multiflorum Preparata.

In another specific embodiment provided by the present invention, the traditional Chinese medicine composition is made from the following raw materials in specified portions by weight: 20 portions of ginseng, 80 portions of Radix paeoniae Alba, 20 portions of Tree Peony Bark, 80 portions of Sharpleaf Galangal Fruit, and 30 portions of Radix Polygonum multiflorum Preparata.

In another specific embodiment provided by the present invention, the traditional Chinese medicine composition is made from the following raw materials in specified portions by weight: 40 portions of ginseng, 60 portions of Radix paeoniae Alba, 40 portions of Tree Peony Bark, 60 portions of Sharpleaf Galangal Fruit, and 40 portions of Radix Polygonum multiflorum Preparata.

The present invention also provides a method for preparing the traditional Chinese medicine composition, comprising the following steps: ginseng, Radix paeoniae Alba, Tree Peony Bark, Sharpleaf Galangal Fruit and Radix Polygonum multiflorum Preparata are mixed and extracted with water to obtain the traditional Chinese medicine composition.

Preferably, in the step of extracting with water: extraction is carried out for totally 2-3 times, the administration amount of boiling water during each extraction is 10-20 folds of the total mass of raw materials, the duration of each extraction is 2-3 h.

In a specific embodiment provided by the present invention, in the step of extracting with water: extraction is carried out for totally 2 times, the administration amount of boiling water during each extraction is 10 folds of the total mass of raw materials, the duration of each extraction is 2 h.

Preferably, it further comprises a step of concentrating the extract prior to obtain the traditional Chinese medicine composition and after extracting with water.

The present invention also provides a health-care food product comprising the traditional Chinese medicine composition provided by the present invention.

In the health-care food product of the present invention, the traditional Chinese medicine composition is formulated into a plurality of dosage forms using a conventional process and excipients. For example, the dosage forms can be tablet, (soft and hard) capsule, granule, powder, oral solution, and medicinal tea, etc.

The present invention also provides a medication comprising the traditional Chinese medicine composition provided by the present invention.

In the medication of the present invention, the traditional Chinese medicine composition is formulated into a plurality of dosage forms using a conventional process and excipients. For example, the dosage forms can be tablet, (soft and hard) capsule, granule, powder, oral solution, and medicinal tea, etc.

The present invention provides a traditional Chinese medicine composition having a function of regulating emotions, a process for preparing the same, and a product thereof. The traditional Chinese medicine composition is made from the following herbal materials in specified portions by weight: 10-100 portions of ginseng, 10-100 portions of Radix paeoniae Alba, 10-100 portions of Tree Peony Bark, 10-100 portions of Sharpleaf Galangal Fruit, and 10-100 portions of Radix Polygonum multiflorum Preparata. The present invention has the following advantages:

The present invention is based on the traditional Chinese medicine theory and made from medicinal and edible raw materials, which are selected by the famous old Chinese medicines according to several decades of clinical experience. After repeated screening and verification by modern pharmacological research methods, it was found that the composition had effects of nourishing liver and kidney, regulating Yin and Yang, tonifying Qi and nourishing blood, and regulating emotions, it also had effects of regulating the release of neurotransmitter and protecting the function of autonomic nerve, and it could improve pressure-induced anxiety and depression, inattention, poor spirit, dispirited, learning and memory capacity decline, etc. The invention has the advantages of specific, remarkable and better effect than the single agent, and has synergistic effect, and it uses all natural medicinal and edible plants as raw materials, the combination of which is simple, safe and stable, and is suitable for long-term use.

EMBODIMENTS

The present invention discloses a traditional Chinese medicine composition having a function of regulating emotions, a process for preparing the same, and a product thereof, which may be implemented with suitable modifications of the process parameters by those skilled in the art in light of the present disclosure. All the similar alterations and modifications are clear to those skilled in the art and deemed to be included in the present invention. Methods and uses of the present invention have been described by the preferred examples, and it is obvious that those in related art are able to make changes or appropriate alternations and the combinations thereof to the methods and uses described herein to implement and apply the inventive technology without departing from the disclosure, spirit and scope of the present invention.

The ingredients or auxiliaries used in the traditional Chinese medicine composition having a function of regulating emotions, a process for preparing the same, and a product thereof in the present invention are all commercially available.

The raw materials used in the above examples including ginseng, Radix paeoniae Alba, Tree Peony Bark, Sharpleaf Galangal Fruit, and Radix Polygonum multiflorum Preparata in accordance with the quality standard of "Chinese Pharmacopoeia (2015)".

The present invention is further explained in combination with the examples below.

Example 1

The traditional Chinese medicine composition having a function of regulating emotions provided by the present example was made from the following herbal materials in specified portions by weight: 60 portions of ginseng, 60 portions of Radix paeoniae Alba, 60 portions of Tree Peony Bark, 45 portions of Sharpleaf Galangal Fruit, and 45 portions of Radix Polygonum multiflorum Preparata.

The preparation method comprised the following steps: weighting ginseng 60 g, Radix paeoniae Alba 60 g, Tree Peony Bark 60 g, Sharpleaf Galangal Fruit 45 g, and Radix Polygonum multiflorum Preparata 45 g, conducting decoction with 10 folds of boiling water for 2 hours, extracting twice and combining the filtrate, concentrating to 300 mL.

Experimental Example 1

Pharmacodynamic Studies

In order to confirm the efficacy of the Chinese herbal medicine composition provided by Example 1 of the present invention, the inventor prepared the water extract by the conventional process using the raw material ratio provided in the above Example 1, and conducted the efficacy test. The results were as follows:

1. Experimental Purpose

To investigate the effect of the Chinese herbal medicine extract on relieving anxiety and depressive symptoms and protecting the function of autonomic nerve.

2. Experimental Materials 2.1 Experimental Sample

According to the raw material ratio provided in Example 1, weighting ginseng 60 g, Radix paeoniae Alba 60 g, Tree Peony Bark 60 g, Sharpleaf Galangal Fruit 45 g, and Radix Polygonum multiflorum Preparata 45 g, conducting decoction with 10 folds of boiling water for 2 hours, extracting twice and combining the filtrate, concentrating to 300 mL.

The preparation method of the extract of each raw material including ginseng, Radix paeoniae Alba, Tree Peony Bark, Sharpleaf Galangal Fruit, and Radix Polygonum multiflorum Preparata was the same as that of the composition of Example 1.

2.2 Modeling and Administration

The rats were housed in individual cages with light and temperature control (temperature: 21±2° C.; lights on at 8:00

AM and off at 8:00 PM). Food and water were available ad libitum. All experimental procedures were carried out in strict accordance with the National Institutes of Health guidelines for care and use of experimental animals. After an initial habituation period of 1 week, all animals were given access to bottle containing a sucrose solution in tap water for 1 hour and were tested for the baseline data of the sucrose preference test. According to the baseline data, the animals were divided into 9 groups (n=10-12 animals/each group), that is the control group, the stressed group, the stressed+ fluoxetine group, the stressed+Example 1 group, the stressed+ginseng extract group, the stressed+Radix paeoniae Alba extract group, the stressed+Tree Peony Bark extract group, the stressed+Sharpleaf Galangal Fruit extract group, and the stressed+Radix Polygonum multiflorum Preparata extract group. The animals were subjected to 2 to 5 different mild stressors per day for 5 weeks. The mild stressors included water and food deprivation, cage tilt, continuously lighting, cage soiling, stroboscopic lighting, restricted access to food, and tail pinching. Control animals were not subjected to the stress protocol, and the stressed animals were subjected to the mild stressors and given the same amount of water as control group. The animals of the stressed+fluoxetine group were subjected to the mild stressors and treated with fluoxetine capsules. The animals of the stressed+Example 1 group were subjected to the mild stressors and treated with the composition of Example 1. The animals of the stressed+single extract group were subjected to the mild stressors and treated with the single extract.

2.3 Sucrose Preference Test

The rats could select between two bottles of liquid freely, one with 0.8% sucrose solution and one with tap water, after 23 h food and water deprivation. To avoid the rats prefer to drink one side of the water, the position of the two bottles were exchanged every half an hour. Tap water consumption and sucrose consumption were measured by weighting the bottles, and the sucrose preference were calculated based on the following formula:

$$SP = \frac{\text{sucrose intake (g)}}{\text{sucrose intake (g)} + \text{water intake (g)}} \times 100\%$$

2.4 Neurotransmitter Measurement

The rats were sacrificed and the trunk blood was collected into the collection tubes coated with standard heparin. The collection tubes were centrifuged in 4° C. centrifugal machine at 3000 rpm for 15 min. The supernatant was collected and stored at −20° C. until analysis. The levels of corticotropin-releasing hormone (CRH), adrenocorticotropic hormone (ACTH) and cortisol (CORT) were detected by ELISA.

3. Experimental Results 3.1 Results of Sucrose Preference Test

According to compare the sucrose preference after the stress experiment of each group (as shown in Table 1), it was found that fluoxetine and Example 1 could significantly increase the sucrose preference compared with the stressed group, and it indicated that Example 1 had the effect of improving the symptoms of anhedonia in the chronically stressed rats, and the efficacy was superior to the single herb extract.

TABLE 1

The effect of Example 1 on the sucrose preference of chronically stressed rats

| Group | Number of Animals | Sucrose Preferenc |
|---|---|---|
| control group | 11 | 0.7694 ± 0.0295 |
| stressed group | 10 | 0.6054 ± 0.0633* |
| stressed + fluoxetine group | 12 | 0.7431 ± 0.0565[#] |
| stressed + Example 1 group | 12 | 0.7384 ± 0.0702[#] |
| stressed + ginseng extract group | 12 | 0.6534 ± 0.0740[#] |
| stressed + Radix paeoniae Alba extract group | 12 | 0.6101 ± 0.0423 |
| stressed + Tree Peony Bark extract group | 12 | 0.6043 ± 0.0735 |
| stressed + Sharpleaf Galangal Fruit extract group | 12 | 0.6632 ± 0.0242# |
| stressed + Radix Polygonum multiflorum Preparata extract group | 12 | 0.6078 ± 0.0345 |

3.2 Results of Neurotransmitter Measurement

As shown in Table 2, the results of neurotransmitter measurement were indicated that chronic stress could significantly increase CRH levels in rats, and significantly reduce ACTH and CORT levels in rats. Fluoxetine and Example 1 could improve the abnormal levels of CRH, ACTH and CORT caused by chronic stress, and it indicated that Example 1 had a certain neuroprotective effect, and the efficacy of it was superior to each of the single herb extract.

TABLE 2

The effect of Example 1 on the neurotransmitter of chronically stressed rats

| Group | Number of Animals | CRH (ng/ml) | ACTH (pg/ml) | CORT (ng/ml) |
|---|---|---|---|---|
| control group | 10 | 5.01 ± 0.38 | 34.15 ± 4.27 | 53.73 ± 5.54 |
| stress group | 10 | 5.97 ± 0.36* | 25.45 ± 2.68* | 42.34 ± 4.94* |
| stressed + fluoxetine group | 10 | 5.13 ± 0.25[#] | 33.83 ± 2.26[#] | 52.09 ± 5.95[#] |
| stressed + Example 1 group | 10 | 5.16 ± 0.29[#] | 33.28 ± 3.75[#] | 54.08 ± 1.84[#] |
| stressed + ginseng extract group | 12 | 5.82 ± 0.33 | 26.34 ± 3.45 | 50.01 ± 3.34[#] |
| stressed + Radix paeoniae Alba extract group | 12 | 5.69 ± 0.58 | 28.23 ± 1.89 | 43.22 ± 5.34 |
| stressed + Tree Peony Bark extract group | 12 | 5.76 ± 0.66 | 27.67 ± 2.31 | 45.15 ± 5.01 |
| stressed + Sharpleaf Galangal Fruit extract group | 12 | 5.61 ± 0.40 | 30.03 ± 2.53[#] | 51.23 ± 3.32[#] |

TABLE 2-continued

The effect of Example 1 on the neurotransmitter of chronically stressed rats

| Group | Number of Animals | CRH (ng/ml) | ACTH (pg/ml) | CORT (ng/ml) |
|---|---|---|---|---|
| stressed + Radix Polygonum multiflorum Preparata extract group | 12 | 5.65 ± 0.31 | 29.34 ± 5.43# | 46.04 ± 2.35 |

Notes:
*presents a comparison to control group, $p < 0.05$;
presents a comparison to model group, $p < 0.05$.

4. Summary of Efficacy

As shown in the above experiments, Example 1 could improve anhedonia in chronically stressed rat model and the abnormal levels of the neurotransmitter, and it had a significant effect of modulating mood and protecting the function of nervous system. Meanwhile, the experimental results indicated that the combination of ginseng, Radix paeoniae Alba, Tree Peony Bark, Sharpleaf Galangal Fruit, and Radix Polygonum multiflorum Preparata had a certain synergistic effect.

Example 2

The traditional Chinese medicine composition having a function of regulating emotions provided by the present invention was made from the following herbal materials in specified portions by weight: 80 portions of ginseng, 80 portions of Radix paeoniae Alba, 80 portions of Tree Peony Bark, 20 portions of Sharpleaf Galangal Fruit, and 20 portions of Radix Polygonum multiflorum Preparata.

The preparation method was the same as that of Example 1.

Example 3

The traditional Chinese medicine composition having a function of regulating emotions provided by the present invention was made from the following herbal materials in specified portions by weight: 50 portions of ginseng, 50 portions of Radix paeoniae Alba, 50 portions of Tree Peony Bark, 50 portions of Sharpleaf Galangal Fruit, and 50 portions of Radix Polygonum multiflorum Preparata.

The preparation method was the same as that of Example 1.

Example 4

The traditional Chinese medicine composition having a function of regulating emotions provided by the present invention was made from the following herbal materials in specified portions by weight: 40 portions of ginseng, 40 portions of Radix paeoniae Alba, 40 portions of Tree Peony Bark, 60 portions of Sharpleaf Galangal Fruit, and 60 portions of Radix Polygonum multiflorum Preparata.

The preparation method was the same as that of Example 1.

Example 5

The traditional Chinese medicine composition having a function of regulating emotions provided by the present invention was made from the following herbal materials in specified portions by weight: 60 portions of ginseng, 60 portions of Radix paeoniae Alba, 60 portions of Tree Peony Bark, 40 portions of Sharpleaf Galangal Fruit, and 60 portions of Radix Polygonum multiflorum Preparata.

The preparation method was the same as that of Example 1.

Example 6

The traditional Chinese medicine composition having a function of regulating emotions provided by the present invention was made from the following herbal materials in specified portions by weight: 20 portions of ginseng, 80 portions of Radix paeoniae Alba, 20 portions of Tree Peony Bark, 80 portions of Sharpleaf Galangal Fruit, and 20 portions of Radix Polygonum multiflorum Preparata.

The preparation method was the same as that of Example 1.

Example 7

The traditional Chinese medicine composition having a function of regulating emotions provided by the present invention was made from the following herbal materials in specified portions by weight: 40 portions of ginseng, 60 portions of Radix paeoniae Alba, 40 portions of Tree Peony Bark, 60 portions of Sharpleaf Galangal Fruit, and 40 portions of Radix Polygonum multiflorum Preparata.

The preparation method was the same as that of Example 1.

Experimental Example 2

Pharmacodynamic Studies

In order to confirm the efficacy of the Chinese herbal medicine composition provided by Examples 2-7 of the present invention, the inventor prepared the water extract by the conventional process using the raw material ratio provided in the above Example 2-7, and conducted the efficacy test. The results were as follows:

1. Experimental Purpose

To investigate the effect of the Chinese herbal medicine extract on relieving anxiety and depressive symptoms and protecting the function of autonomic nerve.

2. Experimental Materials 2.1 Experimental Sample

The extract of Examples 2-7.

2.2 Modeling and Administration

The rats were housed in individual cages with light and temperature control (temperature: 21±2° C.; lights on at 8:00 AM and off at 8:00 PM). Food and water were available ad libitum. All experimental procedures were carried out in strict accordance with the National Institutes of Health guidelines for care and use of experimental animals. After an initial habituation period of 1 week, all animals were given access to bottle containing a sucrose solution in tap water for 1 hour and were tested for the baseline data of the sucrose preference test. According to the baseline data, the animals were divided into 9 groups (n=10-12 animals/each group), that is the control group, the stressed group, the stressed+fluoxetine group, the stressed+Example 2 group, the stressed+Example 3 group, the stressed+Example 4 group, the stressed+Example 5 group, the stressed+Example 6 group, and the stressed+Example 7 group. The animals were subjected to 2 to 5 different mild stressors per day for 5 weeks. The mild stressors included water and food deprivation, cage tilt, continuously lighting, cage soiling, stroboscopic lighting, restricted access to food, and tail pinching. Control animals were not subjected to the stressed protocol, and stressed animals were subjected to the mild stressors and given the same amount of water as control group. The animals of the stressed+fluoxetine group were subjected to the mild stressors and treated with fluoxetine capsules. The animals of the stressed+Example 2-7 groups were subjected to the mild stressors and treated with the compositions of Example 2-7.

2.3 Sucrose Preference Test

The rats could select between two bottles of liquid freely, one with 0.8% sucrose solution and one with tap water, after 23 h food and water deprivation. To avoid the rats prefer to drink one side of the water, the position of the two bottles were exchanged every half an hour. Tap water consumption and sucrose consumption were measured by weighting the bottles, and the sucrose preference were calculated based on the following formula:

$$SP = \frac{\text{sucrose intake (g)}}{\text{sucrose intake (g)} + \text{water intake (g)}} \times 100\%$$

2.4 Neurotransmitter Measurement

The rats were sacrificed and the trunk blood was collected into the collection tubes coated with standard heparin. The collection tubes were centrifuged in 4° C. centrifugal machine at 3000 rpm for 15 min. The supernatant was collected and stored at −20° C. until analysis. The levels of corticotropin-releasing hormone (CRH), adrenocorticotropic hormone (ACTH) and cortisol (CORT) were detected by ELISA.

3. Experimental Results 3.1 Results of Sucrose Preference Test

According to compare the sucrose preference after the stress experiment of each group (as shown in Table 3), it was found that fluoxetine and Examples 2-7 could significantly increase the sucrose preference to varying degrees compared with the stressed group, and it indicated that Example 2-7 had the effect of improving the symptoms of anhedonia in the chronically stressed rats.

TABLE 3

The effects of Example 2-7 on the sucrose preference of chronically stressed rats

| Group | Number of Animals | Sucrose Preference |
|---|---|---|
| control group | 11 | 0.7694 ± 0.0295 |
| stressed group | 10 | 0.6054 ± 0.0633* |
| stressed + fluoxetine group | 12 | 0.7431 ± 0.0565# |
| stressed + Example 2 group | 12 | 0.6462 ± 0.0624 |

TABLE 3-continued

The effects of Example 2-7 on the sucrose preference of chronically stressed rats

| Group | Number of Animals | Sucrose Preference |
|---|---|---|
| stressed + Example 3 group | 12 | 0.6962 ± 0.0534# |
| stressed + Example 4 group | 12 | 0.6845 ± 0.0712# |
| stressed + Example 5 group | 12 | 0.7001 ± 0.0213# |
| stressed + Example 6 group | 12 | 0.6221 ± 0.0431 |
| stressed + Example 7 group | 12 | 0.7003 ± 0.0421# |

3.2 Results of Neurotransmitter Measurement

As shown in Table 4, the results of neurotransmitter measurement were indicated that chronic stress could significantly increase CRH levels in rats, and significantly reduce ACTH and CORT levels in rats. Fluoxetine and Example 2-7 could improve the abnormal levels of CRH, ACTH and CORT caused by chronic stress, and it indicated that Example 2-7 had a certain neuroprotective effect.

TABLE 4

The effects of Example 2-7 on the neurotransmitter of chronically stressed rats

| Group | Number of Animals | CRH (ng/ml) | ACTH (pg/ml) | CORT (ng/ml) |
|---|---|---|---|---|
| control group | 10 | 5.01 ± 0.38 | 34.15 ± 4.27 | 53.73 ± 5.54 |
| stressed group | 10 | 5.97 ± 0.36* | 25.45 ± 2.68* | 42.34 ± 4.94* |
| stressed + fluoxetine group | 10 | 5.13 ± 0.25# | 33.83 ± 2.26# | 52.09 ± 5.95# |
| stressed + Example 2 group | 12 | 5.18 ± 0.24# | 28.33 ± 1.98 | 44.01 ± 2.29 |
| stressed + Example 3 group | 12 | 5.53 ± 0.45 | 34.34 ± 2.21# | 51.23 ± 4.03# |
| stressed + Example 4 group | 12 | 5.12 ± 0.24# | 26.12 ± 3.45 | 50.03 ± 4.13# |
| stressed + Example 5 group | 12 | 5.78 ± 0.29 | 30.13 ± 5.12# | 54.23 ± 3.21# |
| stressed + Example 6 group | 12 | 5.59 ± 0.39 | 29.12 ± 4.23# | 43.24 ± 3.56 |
| stress + Example 7 group | 12 | 5.07 ± 0.21# | 24.36 ± 4.01 | 51.98 ± 6.39# |

Notes:
*presents a comparison to control group, p < 0.05;
presents a comparison to model group, p < 0.05.

4. Summary of Efficacy

As shown in the above experiments, Examples 2-7 could improve anhedonia in chronic stress rat model and the abnormal levels of the neurotransmitter, and it had an effect of modulating mood and protecting the function of nervous system. Meanwhile, the experimental results indicated that the combination of ginseng, Radix paeoniae Alba, Tree Peony Bark, Sharpleaf Galangal Fruit, and Radix Polygonum multiflorum Preparata had a certain synergistic effect.

Comparative Example 1

The traditional Chinese medicine composition having a function of regulating emotions provided by the present comparative example was made from the following herbal materials in specified portions by weight: 10 portions of ginseng, 120 portions of Radix paeoniae Alba, 10 portions of Tree Peony Bark, 120 portions of Sharpleaf Galangal Fruit, and 10 portions of Radix Polygonum multiflorum Preparata.

The preparation method was the same as that of Example 1.

Comparative Example 2

The traditional Chinese medicine composition having a function of regulating emotions provided by the present comparative example was made from the following herbal materials in specified portions by weight: 120 portions of ginseng, 10 portions of Radix paeoniae Alba, 120 portions of Tree Peony Bark, 10 portions of Sharpleaf Galangal Fruit, and 120 portions of Radix Polygonum multiflorum Preparata.

The preparation method was the same as that of Example 1.

Comparative Example 3

The traditional Chinese medicine composition having a function of regulating emotions provided by the present comparative example was made from the following herbal materials in specified portions by weight: 60 portions of Radix paeoniae Alba, 60 portions of Tree Peony Bark, 45 portions of Sharpleaf Galangal Fruit, and 45 portions of Radix Polygonum multiflorum Preparata.

The preparation method was the same as that of Example 1.

Comparative Example 4

The traditional Chinese medicine composition having a function of regulating emotions provided by the present comparative example was made from the following herbal materials in specified portions by weight: 60 portions of ginseng, 60 portions of Tree Peony Bark, 45 portions of Sharpleaf Galangal Fruit, and 45 portions of Radix Polygonum multiflorum Preparata.

The preparation method was the same as that of Example 1.

Comparative Example 5

The traditional Chinese medicine composition having a function of regulating emotions provided by the present comparative example was made from the following herbal materials in specified portions by weight: 60 portions of ginseng, 60 portions of Radix paeoniae Alba, 45 portions of Sharpleaf Galangal Fruit, and 45 portions of Radix Polygonum multiflorum Preparata.

The preparation method was the same as that of Example 1.

Comparative Example 6

The traditional Chinese medicine composition having a function of regulating emotions provided by the present comparative example was made from the following herbal materials in specified portions by weight: 60 portions of ginseng, 60 portions of Radix paeoniae Alba, 60 portions of Tree Peony Bark, and 45 portions of Radix Polygonum multiflorum Preparata.

The preparation method was the same as that of Example 1.

Comparative Example 7

The traditional Chinese medicine composition having a function of regulating emotions provided by the present comparative example was made from the following herbal materials in specified portions by weight: 60 portions of ginseng, 60 portions of Radix paeoniae Alba, 60 portions of Tree Peony Bark, and 45 portions of Sharpleaf Galangal Fruit.

The preparation method was the same as that of Example 1.

Comparative Example 1

Pharmacodynamic Studies

In order to confirm the efficacy of the Chinese herbal medicine composition provided by Comparative Example 1-7 of the present invention, the inventor prepared the water extract by the conventional process using the raw material ratio provided in the above Comparative Example 1-7, and conducted the efficacy test. The results were as follows:

1. Experimental Purpose

To investigate the effect of the Chinese herbal medicine extract on relieving anxiety and depressive symptoms and protecting the function of autonomic nerve.

2. Experimental Materials 2.1 Experimental Sample

The extract of Comparative Example 1-7.

2.2 Modeling and Administration

The rats were housed in individual cages with light and temperature control (temperature: 21±2° C.; lights on at 8:00 AM and off at 8:00 PM). Food and water were available ad libitum. All experimental procedures were carried out in strict accordance with the National Institutes of Health guidelines for care and use of experimental animals. After an initial habituation period of 1 week, all animals were given access to bottle containing a sucrose solution in tap water for 1 hour and were tested for the baseline data of the sucrose preference test. According to the baseline data, the animals were divided into 10 groups (n=10-12 each), that is the control group, the stressed group, the stressed+fluoxetine group, the stressed+Comparative Example 1 group, the stressed+Comparative Example 2 group, the stressed+Comparative Example 3 group, the stressed+Comparative Example 4 group, the stressed+Comparative example 5 group, the stressed+Comparative Example 6 group, and the stressed+Comparative Example 7 group. The animals were subjected to 2 to 5 different mild stressors per day for 5 weeks. The mild stressors included water and food deprivation, cage tilt, continuously lighting, cage soiling, stroboscopic lighting, restricted access to food, and tail pinching. Control animals were not subjected to the stress protocol, and stressed animals were subjected to the mild stressors and given the same amount of water as control group. The animals of the stressed+fluoxetine group were subjected to the mild stressors and treated with fluoxetine capsules. The animals of the stressed+Comparative Example 1-7 groups were subjected to the mild stressors and treated with the compositions of Comparative Example 1-7.

2.3 Sucrose Preference Test

The rats could select between two bottles of liquid freely, one with 0.8% sucrose solution and one with tap water after 23 h food and water deprivation. To avoid the rats prefer to drink one side of the water, the position of the two bottles were exchanged every half an hour. Tap water consumption and sucrose consumption were measured by weighting the bottles, and the sucrose preference were calculated based on the following formula:

$$SP = \frac{\text{sucrose intake (g)}}{\text{sucrose intake (g)} + \text{water intake (g)}} \times 100\%$$

2.4 Neurotransmitter Measurement

The rats were sacrificed and the trunk blood was collected into the collection tubes coated with standard heparin. The collection tubes were centrifuged in 4° C. centrifugal machine at 3000 rpm for 15 min. The supernatant was collected and stored at −20° C. until analysis. The levels of corticotropin-releasing hormone (CRH), adrenocorticotropic hormone (ACTH) and cortisol (CORT) were detected by ELISA.

3. Experimental Results

3.1 Results of Sucrose Preference Test

According to compare the sucrose preference after the stress experiment of each group (as shown in Table 5), it was found that fluoxetine could significantly increase the sucrose preference compared with the stress group, and it had the effect of improving the symptoms of anhedonia, but comparing with stress group, the sucrose preference of Comparative Example 1-7 were not changed significantly.

TABLE 5

The effects of Comparative Example 1-7 on the sucrose preference of chronically stressed rats

| Group | Number of Animals | Sucrose Preference |
| --- | --- | --- |
| control group | 11 | 0.8204 ± 0.0195 |
| stress group | 10 | 0.5901 ± 0.0433* |
| stress + fluoxetine group | 12 | 0.7502 ± 0.0471[#] |
| stress + Comparative Example 1 group | 12 | 0.6134 ± 0.0453 |
| stress + Comparative Example 2 group | 12 | 0.6212 ± 0.0212 |
| stress + Comparative Example 3 group | 12 | 0.5801 ± 0.0534 |
| stress + Comparative Example 4 group | 12 | 0.6121 ± 0.0321 |
| stress + Comparative Example 5 group | 12 | 0.6019 ± 0.0521 |
| stress + Comparative Example 6 group | 12 | 0.6047 ± 0.0529 |
| stress + Comparative Example 7 group | 12 | 0.6081 ± 0.0487 |

3.2 Results of Neurotransmitter Measurement

As shown in Table 6, the results of neurotransmitter measurement were indicated that chronic stress could significantly increase CRH levels in rats, and significantly reduce ACTH and CORT levels in rats. Fluoxetine rather than Comparative Examples 1-7 could improve the abnormal levels of CRH, ACTH and CORT caused by chronic stress.

TABLE 6

The effects of Comparative Examples 1-7 on the neurotransmitter of chronically stressed rats

| Group | Number of Animals | CRH (ng/ml) | ACTH (pg/ml) | CORT (ng/ml) |
| --- | --- | --- | --- | --- |
| control group | 10 | 5.03 ± 0.41 | 33.17 ± 3.26 | 54.73 ± 4.84 |
| stressed group | 10 | 5.88 ± 0.25* | 26.19 ± 2.68* | 41.40 ± 3.98* |
| stressed + fluoxetine group | 10 | 5.11 ± 0.29[#] | 32.73 ± 2.66[#] | 52.46 ± 6.05[#] |
| stressed + Comparative Example 1 group | 12 | 5.86 ± 0.56 | 24.76 ± 2.80 | 43.39 ± 3.45 |
| stressed + Comparative Example 2 group | 12 | 5.90 ± 0.21 | 25.65 ± 1.98 | 44.48 ± 3.57 |
| stressed + Comparative Example 3 group | 12 | 6.01 ± 0.22 | 27.01 ± 1.02 | 42.33 ± 3.01 |
| stressed + Comparative Example 4 group | 12 | 5.98 ± 0.29 | 25.10 ± 2.98 | 42.88 ± 2.10 |
| stressed + Comparative Example 5 group | 12 | 5.84 ± 0.24 | 25.39 ± 3.11 | 43.29 ± 1.99 |
| stressed + Comparative Example 6 group | 12 | 5.93 ± 0.38 | 26.18 ± 2.01 | 41.90 ± 3.42 |
| stresse + Comparative Example 7 group | 12 | 5.66 ± 0.78 | 26.16 ± 2.81 | 43.39 ± 2.01 |

Notes:

*presents a comparison to control group, $p < 0.05$;

[#]presents a comparison to model group, $p < 0.05$.

The above description gives only the preferred embodiments of the present invention, and it should be noted that for those of ordinary skill in the art, a number of improvements and modifications can be made without departing from the principle of the invention, which are also regarded as falling into the scope claimed in the present invention.

The invention claimed is:

1. A traditional Chinese medicine composition in a dose effective for alleviating stress, the composition made from raw materials consisting of, in specified parts by weight: 40-60 parts of ginseng, 40-60 parts of Radix paeoniae Alba, 40-60 parts of Tree Peony Bark, 40-60 parts of Sharpleaf Galangal Fruit, and 40-60 parts of Radix Polygonum multiflorum Preparata.

2. The traditional Chinese medicine composition according to claim 1, wherein the raw materials consist of, in specified parts by weight: 60 parts of ginseng, 60 parts of Radix paeoniae Alba, 60 parts of Tree Peony Bark, 45 parts of Sharpleaf Galangal Fruit, and 45 parts of Radix Polygonum multiflorum Preparata.

3. A method of alleviating stress in a subject, comprising administrating an effective amount of the composition of claim 1 to a subject in need thereof.

* * * * *